US008842851B2

(12) United States Patent
Beaucoup

(10) Patent No.: US 8,842,851 B2
(45) Date of Patent: Sep. 23, 2014

(54) AUDIO SOURCE LOCALIZATION SYSTEM AND METHOD

(75) Inventor: Franck Beaucoup, Vancouver (CA)

(73) Assignee: Broadcom Corporation, Irvine, CA (US)

( * ) Notice: Subject to any disclaimer, the term of this patent is extended or adjusted under 35 U.S.C. 154(b) by 1304 days.

(21) Appl. No.: 12/627,406

(22) Filed: Nov. 30, 2009

(65) Prior Publication Data

US 2010/0150360 A1 Jun. 17, 2010

Related U.S. Application Data

(60) Provisional application No. 61/122,176, filed on Dec. 12, 2008.

(51) Int. Cl.

| | |
|---|---|
| ***H04R 29/00*** | (2006.01) |
| ***A61F 11/06*** | (2006.01) |
| ***G10K 11/16*** | (2006.01) |
| ***H03B 29/00*** | (2006.01) |
| ***H04R 3/00*** | (2006.01) |
| ***H02B 1/00*** | (2006.01) |
| ***H04S 7/00*** | (2006.01) |

(52) U.S. Cl.
CPC . *H04S 7/30* (2013.01); *H04R 3/005* (2013.01)
USPC ............. 381/92; 381/56; 381/71.1; 381/71.2; 381/122; 381/123

(58) Field of Classification Search
CPC ...... H04R 3/005; H04R 1/406; H04R 25/407; H04R 25/405
USPC ........... 381/58, 92, 56, 66, 71.2, 79, 122, 123
See application file for complete search history.

(56) References Cited

U.S. PATENT DOCUMENTS

| | | | | |
|---|---|---|---|---|
| 6,317,501 | B1 * | 11/2001 | Matsuo | 381/92 |
| 2008/0192955 | A1 * | 8/2008 | Merks | 381/92 |

OTHER PUBLICATIONS

Pending U.S. Appl. No. 12/566,329, filed Sep. 24, 2009, 39 pages.

* cited by examiner

*Primary Examiner* — Vivian Chin
*Assistant Examiner* — Douglas Suthers
(74) *Attorney, Agent, or Firm* — Fiala & Weaver P.L.L.C.

(57) ABSTRACT

Systems and methods are described that perform audio source localization in a manner that provides increased robustness and responsiveness in the presence of acoustic echo. The systems and methods calculate a difference between a signal level associated with one or more of the audio signals generated by a microphone array and an estimated level of acoustic echo associated with one or more of the audio signals. This information is then used to determine whether and/or how to perform audio source localization. For example, a controller may use the difference to determine whether or not to freeze an audio source localization module that operates on the audio signals. As another example, the audio source localization module may incorporate the difference (or the estimated level of acoustic echo used to calculate the difference) into the logic that is used to determine the location of a desired audio source.

20 Claims, 13 Drawing Sheets

AUDIO SOURCE LOCALIZATION SYSTEM AND METHOD

CROSS-REFERENCE TO RELATED APPLICATIONS

This application claims priority to U.S. Provisional Patent Application No. 61/122,176, filed Dec. 12, 2008, the entirety of which is incorporated by reference herein.

BACKGROUND OF THE INVENTION

1. Field of the Invention

The present invention relates to systems that automatically determine the location of one or more desired audio sources based on audio input received via an array of microphones.

2. Background

As used herein, the term audio source localization refers to a technique for automatically determining the location of at least one desired audio source, such as a talker, in a room or other area. FIG. 1 is a block diagram of an example system 100 that performs audio source localization. System 100 may represent, for example and without limitation, a speakerphone, a teleconferencing system, a video gaming system, or other system capable of both capturing and playing back audio signals.

As shown in FIG. 1, system 100 includes an output audio processing module 102 that processes at least one audio signal for playback via loudspeakers 104. The audio signal processed by audio output processing module 102 may be received from a remote audio source such as a far-end talker in a speakerphone or teleconferencing scenario. Additionally or alternatively, the audio signal processed by output audio processing module 102 may be generated by system 100 itself or some other source connected locally thereto. For example, in a video gaming scenario, the audio signal processed by output audio processing module 102 may represent music and/or sound effects associated with a video game being executed by system 100.

As further shown in FIG. 1, system 100 further includes an array of microphones 106 that converts sound waves produced by local audio sources into audio signals. These audio signals are then processed by an audio source localization module 108. Depending upon the implementation, the audio signals generated by microphone array 106 may first be processed by other logic (e.g., acoustic echo cancellers (AECs)) prior to being received by audio source localization module 108.

Audio source localization module 108 periodically processes the audio signals generated by microphone array 106 to estimate a current location of a desired audio source 114. Desired audio source 114 may represent, for example, a near-end talker in a speakerphone or teleconferencing scenario or a video game player in a video gaming scenario. The estimated current location of desired audio source 114 as determined by audio source localization module 108 may be defined, for example, in terms of an estimated current direction of arrival of sound waves emanating from desired audio source 114.

System 100 also includes a steerable beamformer 110 that is configured to process the audio signals generated by microphone array 106 to produce a single audio signal. In producing the audio signal, steerable beamformer 110 performs spatial filtering based on the estimated current location of desired audio source 114 such that signal components attributable to sound waves emanating from locations other than the estimated current location of desired audio source 114 are attenuated relative to signal components attributable to sound waves emanating from the estimated current location of desired audio source 114. This tends to have the beneficial effect of attenuating undesired audio sources relative to desired audio source 114, thereby improving the overall quality and intelligibility of the output audio signal. In a speakerphone or teleconferencing scenario, the audio signal produced by steerable beamformer 110 is transmitted to a far-end listener.

The information produced by audio source localization module 108 may also be useful for applications other than steering a beamformer used for acoustic transmission. For example, the information produced by audio source localization module 108 may be used in a video gaming system to integrate the estimated current location of a player within a room into the context of a game (e.g., by controlling the placement of an avatar that represents the player within a scene rendered by a video game based on the estimated current location of the player) or to perform proper sound localization in surround sound gaming applications. Various other beneficial applications of audio source localization also exist. These applications are generally represented in system 100 by the element labeled "other applications" and marked with reference numeral 112.

One problem for system 100 and certain other systems that perform audio source localization is the presence of acoustic echo 116. Acoustic echo 116 is generated when system 100 plays back audio signals via loudspeakers 104, an echo of which is picked up by microphone array 106. In a speakerphone or teleconferencing system, such echo may be attributable to speech signals representing the voices of one or more far end talkers that are played back by the system. Such echo is typically intermittent. In a video gaming system, the echo may be attributable to music, sound effects, and/or other audio content produced by a game. This type of echo is typically more continuous in nature.

The presence of acoustic echo can cause audio source localization module 108 to perform poorly, since the module may not be able to adequately distinguish between desired audio source 114 whose location is to be determined and the echo. This may cause audio source localization module 108 to incorrectly estimate the location of desired audio source 114.

There are some known techniques that may be used to deal with this issue. For example, acoustic echo cancellation may be performed on each of the microphone input signals using transversal filters. However, there are problems with this approach. For example, transversal filters require time to converge to an accurate acoustic impulse response and during this convergence time, echo cancellation performance may be poor. Furthermore, it is likely that the acoustic echo can never be canceled completely because of factors such as background noise/interference 118 and/or non-linearities associated with system loudspeakers or with other audio processing logic that is located outside of system 100. For example, where system 100 is a video gaming system that is part of a home theater installation, audio output produced by the system may be processed by audio processing logic located in a receiver and/or in external speakers.

These problems may render the acoustic echo cancellation insufficiently robust. As a result, residual echo may be delivered to audio source localization module 108, impairing its performance.

Another approach known in the art is to "freeze" the operation of audio source localization module 108 whenever audio content is being played back by system 100. This ensures that the estimated location of desired audio source 114 will not be changed based on acoustic echo. However, this approach negatively impacts the responsiveness of audio source localization module 108, since that module cannot track the location of desired audio source 114 during periods when audio content is being played back by system 100. Such lack of responsiveness is especially damaging in a video gaming application where the audio played back by the video gaming system may be virtually continuous.

What is needed, then, is a system for performing audio source localization in the presence of acoustic echo that addresses one or more of the aforementioned shortcomings associated with prior art solutions.

BRIEF SUMMARY OF THE INVENTION

Systems and methods are described herein that perform audio source localization in a manner that provides both increased robustness and responsiveness in the presence of acoustic echo as compared to conventional approaches. As will be described in more detail herein, system and methods in accordance with various embodiments of the present invention calculate a difference between a signal level associated with one or more of the audio signals generated by a microphone array and an estimated level of acoustic echo associated with one or more of the audio signals. The systems and methods then use this information to determine whether and/or how to perform audio source localization. For example, a controller may use the difference to determine whether or not to freeze an audio source localization module that operates on the audio signals. As another example, the audio source localization module may incorporate the difference (or the estimated level of acoustic echo used to calculate the difference) into the logic that is used to determine the location of a desired audio source.

By using the difference and/or estimated level of acoustic echo to determine whether and/or how to perform audio source localization, systems and methods in accordance with embodiments of the present invention can advantageously reduce the adverse effect of acoustic echo on the performance of audio source localization, thereby providing improved robustness. Furthermore, by using the difference and/or estimated level of acoustic echo to determine whether and/or how to perform audio source localization, systems and methods in accordance with embodiments of the present invention advantageously allow audio source localization to be performed in the presence of echo, thereby providing improved responsiveness.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

Figure 1:
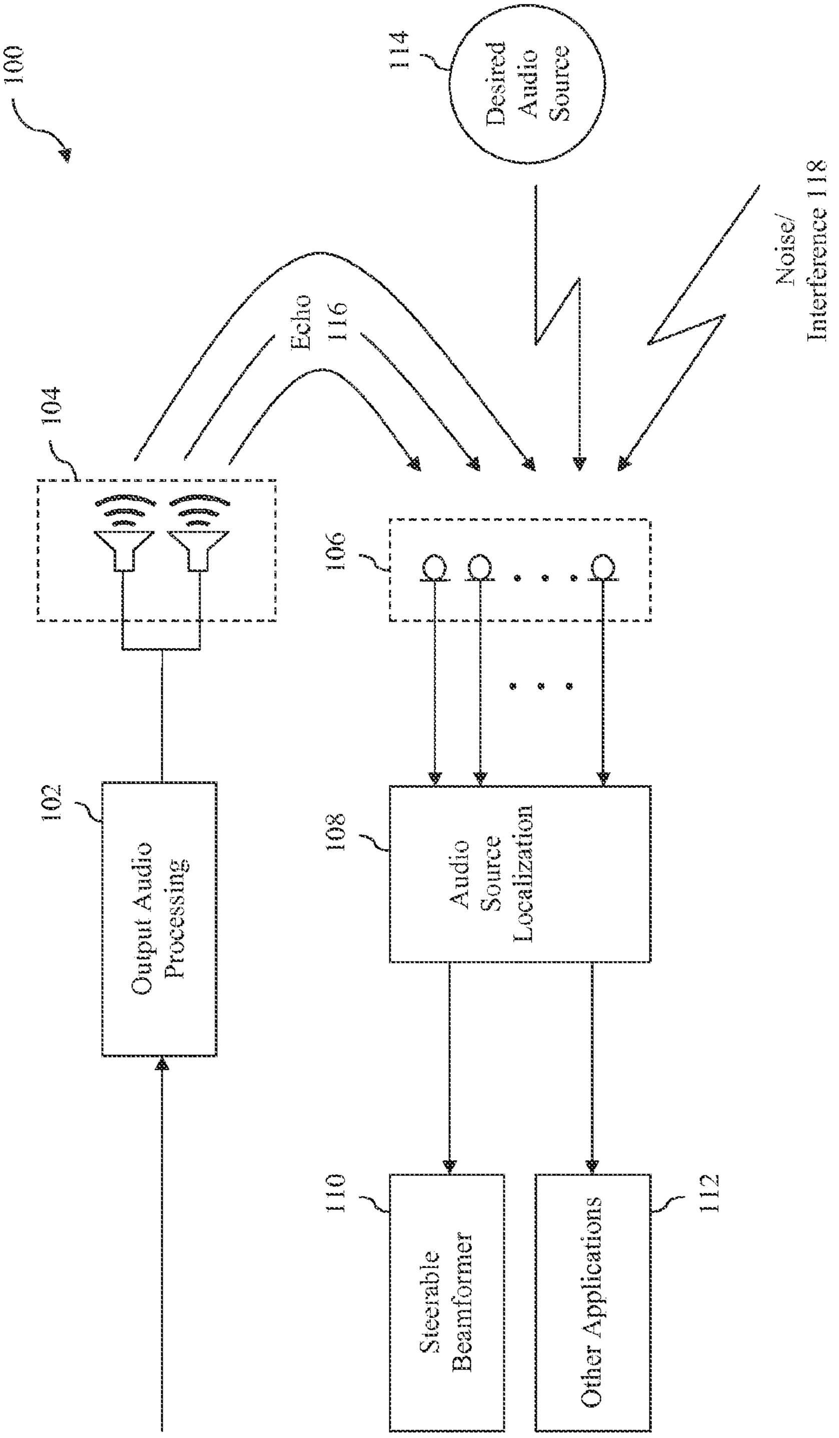
FIG. 1 (Prior Art)
FIG. 1 is a block diagram of an example system that performs audio source localization in a conventional manner.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION OF THE INVENTION

A. Introduction

The following detailed description of the present invention refers to the accompanying drawings that illustrate exemplary embodiments consistent with this invention. Other embodiments are possible, and modifications may be made to the embodiments within the spirit and scope of the present invention. Therefore, the following detailed description is not meant to limit the invention. Rather, the scope of the invention is defined by the appended claims.

References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to implement such feature, structure, or characteristic in connection with other embodiments whether or not explicitly described.

Figure 2:
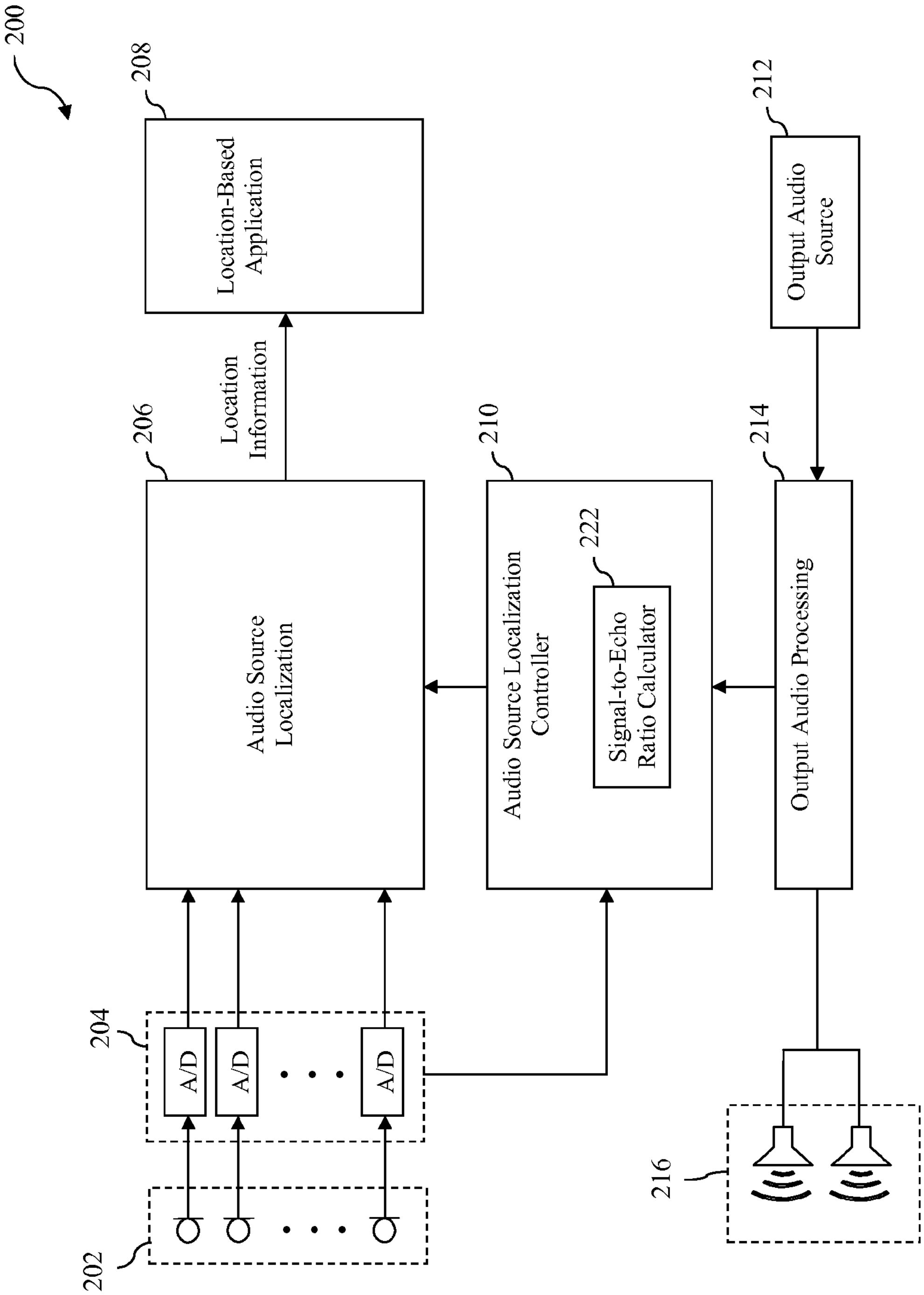
FIG. 2 is a block diagram of a first system that performs audio source localization in accordance with an embodiment of the present invention.

B. First Example System for Performing Audio Source Localization in Accordance with an Embodiment of the Present Invention FIG. 2 is a block diagram of a first example system 200 for performing audio source localization in accordance with an embodiment of the present invention. As shown in FIG. 2, system 200 includes a number of interconnected components including a microphone array 202, an array of analog-to-digital (A/D) converters 204, an audio source localization module 206, a location-based application 208, an audio source localization controller 210, an output audio source 212, an output audio processing module 214, and one or more loudspeakers 216. Each of these components will now be described.

Output audio processing module 214 is configured to receive an audio signal from output audio source 212 and to process the received audio signal for playback via loudspeaker(s) 216. Among other operations, output audio processing module 214 may perform one or more of audio decoding, frame buffering, amplification, and digital-to-analog conversion to generate a processed audio signal that is in a form suitable for playback by loudspeaker(s) 216.

Output audio source 212 is intended to broadly represent any component or entity that is capable of producing an audio signal for playback by system 200. For example, in an embodiment in which system 200 is part of a speakerphone or teleconferencing system, output audio source 212 may comprise a receiver that is configured to receive an audio signal representative of a voice of a far-end talker over a communications network. In an embodiment in which system 200 is part of a video gaming system, output audio source 212 may comprise a video game that, when executed by the appropriate system elements, generates music and/or sound effects for playback. These examples are not intended to be limiting and persons skilled in the relevant art(s) will appreciate that output audio source 212 may represent other types of audio sources as well.

Each of loudspeaker(s) 216 comprises an electro-mechanical transducer that operates in a well-known manner to convert an analog representation of an audio signal into sound waves for perception by a user.

Microphone array 202 comprises two or more microphones that are mounted or otherwise arranged in a manner such that at least a portion of each microphone is exposed to sound waves emanating from audio sources proximally located to system 200. Each microphone in array 202 comprises an acoustic-to-electric transducer that operates in a well-known manner to convert such sound waves into a corresponding analog audio signal. The analog audio signal produced by each microphone in microphone array 202 is provided to a corresponding A/D converter in array 204. Each A/D converter in array 204 operates to convert an analog audio signal produced by a corresponding microphone in microphone array 202 into a digital audio signal comprising a series of digital audio samples prior to delivery to audio source localization module 206.

Audio source localization module 206 is connected to array of A/D converters 204 and receives digital audio signals therefrom. Audio source localization module 206 is configured to periodically process time-aligned segments of the digital audio signals to determine a current location of a desired audio source. A variety of algorithms are known in the art for performing this function. In one example embodiment, audio source localization module 206 is configured to determine the current location of the desired audio source by determining a current direction of arrival (DOA) of sound waves emanating from the desired audio source. After determining the current location of the desired audio source, audio source localization module 206 passes this information to location-based application 208.

Location-based application 208 is intended to broadly represent any application that is configured to perform operations based on the location information received from audio source localization module 206. For example, in an embodiment in which system 200 comprises a speakerphone or teleconferencing system, application 208 may comprise a steerable beamformer that processes the audio signals generated by microphone array 202 to produce a single audio signal for acoustic transmission. In producing the audio signal, the steerable beamformer may perform spatial filtering based on the current location of a desired audio source, such as a desired talker, as determined by audio source localization module 206. As another example, in an embodiment in which system 200 comprises a video teleconferencing system, location-based application 208 may comprise an application that uses the location information provided by audio source localization module 206 to control a video camera to point at and/or zoom in on a desired audio source, such as a desired talker. As a further example, in an embodiment in which system 200 comprises a video gaming system, location-based application 208 may comprise a video gaming application that uses location information provided by audio source localization module 206 to integrate the current location of a player into the context of a game or may comprise a surround sound application that uses location information provided by audio source localization module 206 to perform proper sound localization. These examples are provided by way of illustration only and are not intended to be limiting.

Depending upon the implementation, location-based application 208 may be proximally or remotely located with respect to the other components of system 100. For example, location-based application 208 may be an integrated part of single device that includes the other components of system 100 or may be located in close proximity to the other components of system 100 (e.g., in the same room). Alternatively, location-based application 208 may be located in a different room, home, city or country than the other components of system 100. In either case, a suitable wired or wireless communication link is provided between audio source localization module 206 and location-based application 208 so that location information can be passed there between.

As described in the Background Section above, the performance of audio source localization module 206 may be adversely impacted by acoustic echo generated by sound waves emanating from loudspeaker(s) 216. To address this issue, system 200 includes an audio source localization controller 210. Audio source localization controller 210 selectively enables audio source localization module 206 to produce updated location information when it determines that the impact of acoustic echo upon the performance of the module is likely to be acceptable and selectively disables audio source localization module 206 from producing updated location information when it determines that the impact of acoustic echo upon the performance of the module is likely to be unacceptable. To determine the impact of acoustic echo upon the performance of audio source localization module 206, audio source localization controller includes a signal-to-echo ratio (SER) calculator 222 that calculates at least one SER upon which the disabling/enabling decision is premised. To calculate the at least one SER, SER calculator 222 uses information obtained from output audio processing module 214 and array of A/D converters 204.

The operation of audio source localization controller 210 and SER calculator 222 in accordance with one embodiment of the present invention will now be explained with reference to flowchart 300 of FIG. 3. Although the method of flowchart 300 will be described herein with reference to components of example system 200, it is to be understood that the method is not limited to that implementation and may be performed by other components or systems entirely.

Figure 3:
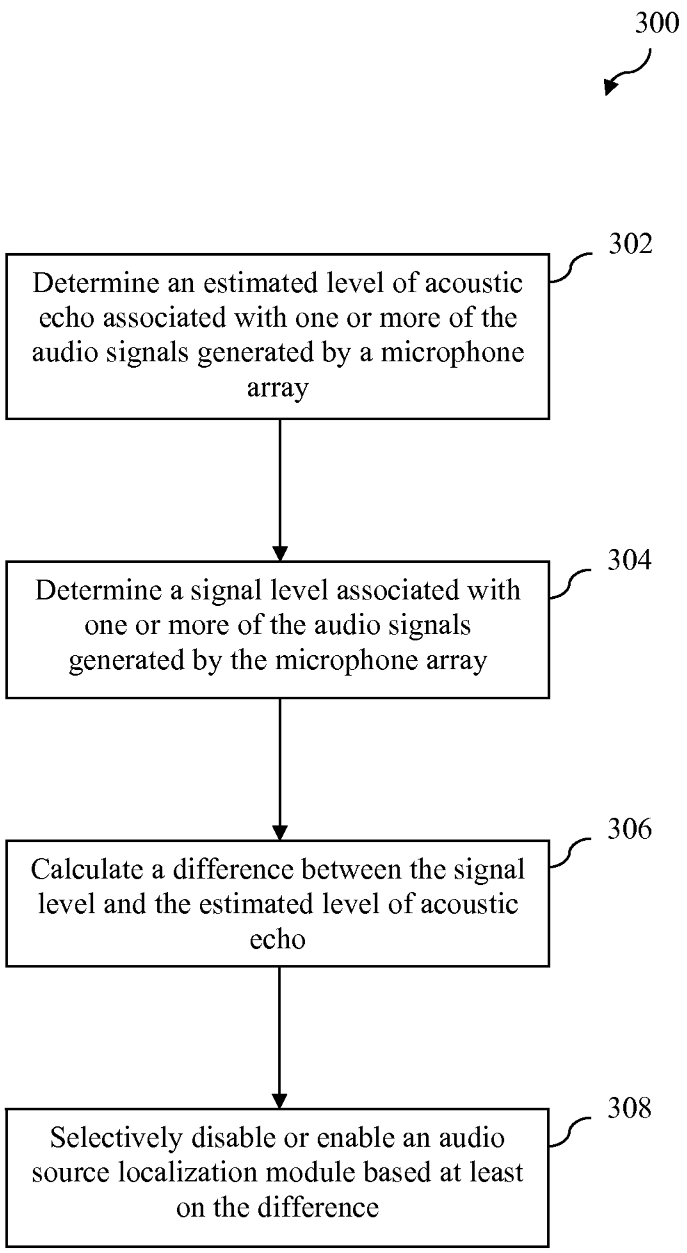
FIG. 3 depicts a flowchart of method for selectively disabling and enabling an audio source localization module in accordance with an embodiment of the present invention.

As shown in FIG. 3, the method of flowchart 300 begins at step 302 in which SER calculator 222 determines an estimated level of acoustic echo associated with one or more of the audio signals generated by microphone array 202. In one embodiment, SER calculator 222 performs this function by estimating an echo return loss (ERL) associated with one or more of the audio signals generated by microphone array 202 and then subtracting in the log domain the estimated ERL from a level of an output audio signal that is processed by output audio processing module 214 for playback via loudspeaker(s) 216. Various methods for determining an ERL are known in the art and thus need not be described herein. In one implementation, the level of the audio signal that is processed by output audio processing module 214 for playback via loudspeaker(s) is measured by output audio processing module 214 and passed to SER calculator 222.

At step 304, SER calculator 222 determines a signal level associated with one or more of the audio signals generated by microphone array 202. The signal level may comprise, for example, the level of an audio signal generated by a designated microphone within microphone array 202 or an average of the levels of the audio signals generated by two or more of the microphones within microphone array 202. The digital representation of the microphone signals produced by array of A/D converters 204 may be used to perform the necessary signal level measurements.

At step 306, SER calculator 222 calculates a difference between the signal level determined during step 304 and the estimated level of acoustic echo determined during step 302 in the dB domain. As will be appreciated by persons skilled in the relevant art(s), this operation is the mathematical equivalent of calculating a ratio between the signal level and the estimated level of acoustic echo in the linear domain.

At step 308, audio source localization controller 210 selectively disables or enables audio source localization module 206 based at least on the difference calculated during step 306. This step may include, for example, selectively disabling or enabling audio source localization module 206 based at least on a determination of whether the difference exceeds a threshold.

Depending upon the implementation, disabling audio source localization module 206 may comprise, for example, preventing audio source localization module 206 from determining a new current location of a desired audio source or preventing audio source localization module 206 from providing a new current location of a desired audio source to location-based application 208. In either case, the effect is to "freeze" the output of audio source localization module 206 such that the determined location of the desired audio source will not change. Conversely, enabling audio source localization module 206 may comprise, for example, enabling audio source localization module 206 to determine a new current location of a desired audio source or enabling audio source localization module 206 to provide a new current location of a desired audio source to location-based application 208.

The foregoing embodiment thus uses at least one SER to determine if the proportion of acoustic echo present in the audio input being received via microphone array 202 is small enough such that module 206 can use the audio input to perform audio source localization in a reliable manner. If it is, then module 206 is enabled and if it is not, module 206 is disabled. This helps to ensure that the location information produced by audio source localization module 206 is reliable even when the module is operating in the presence of acoustic echo. Furthermore, in contrast to certain prior art solutions, this advantageously allows audio source localization to be performed even when an output audio signal is being played back via loudspeaker(s) 216.

Figure 4:
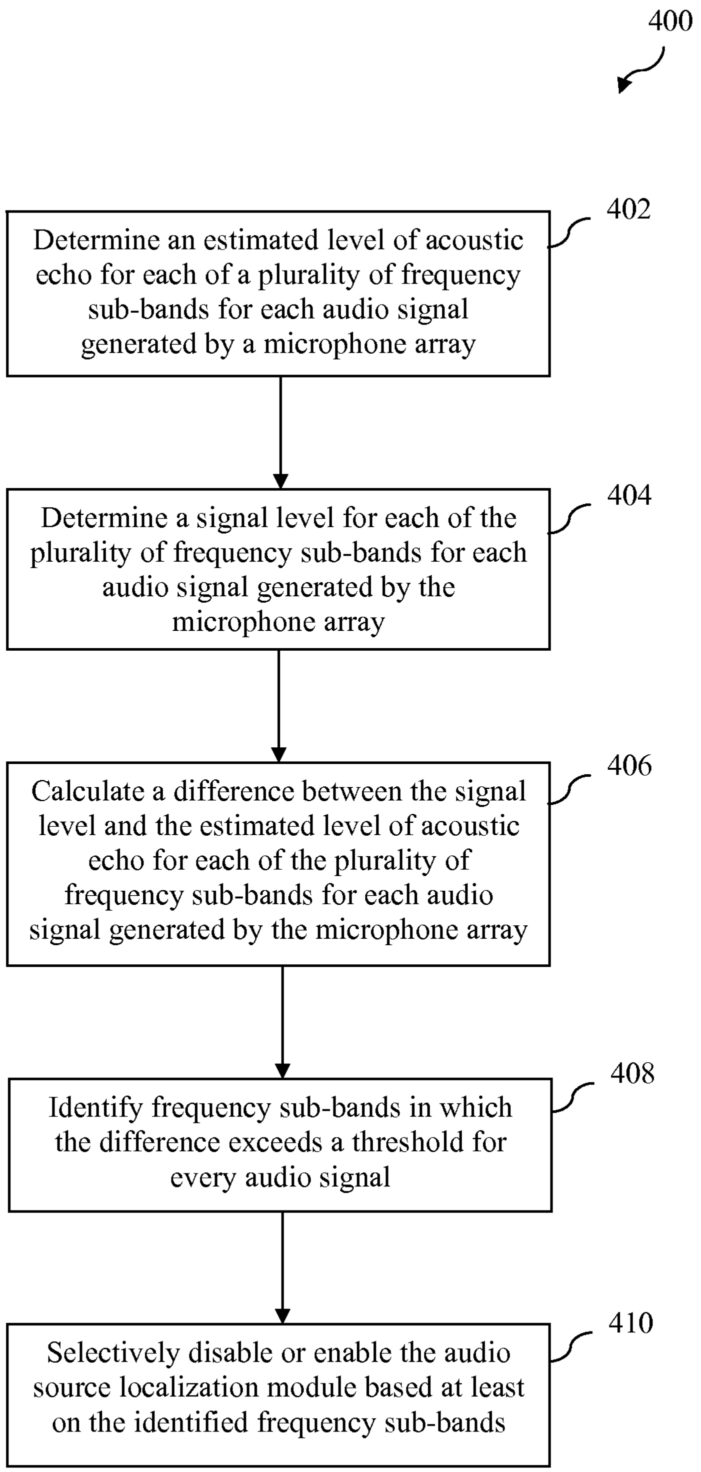
FIG. 4 depicts a flowchart of a particular method for implementing the general method of the flowchart depicted in FIG. 3.

FIG. 4 depicts a flowchart 400 of one particular technique for implementing the general method of flowchart 300 of FIG. 3. The method of flowchart 400 is provided herein by way of example only and is not intended to be limiting. Persons skilled in the relevant art(s) will appreciate that other techniques may be used to implement the general method of flowchart 300 of FIG. 3. Furthermore, although the method of flowchart 400 will also be described herein with continued reference to components of example system 200, it is to be understood that the method is not limited to that implementation and may be performed by other components or systems entirely.

As shown in FIG. 4, the method of flowchart 400 begins at step 402 in which SER calculator 222 determines an estimated level of acoustic echo for each of a plurality of frequency sub-bands for each of the audio signals generated by microphone array 202. In one embodiment, SER calculator 222 performs this function by estimating an ERL for each of the plurality of frequency sub-bands for each of the audio signals generated by microphone array 202. Then for each audio signal, SER estimator 222 subtracts the estimated ERL for each frequency sub-band for that audio signal from a corresponding frequency sub-band signal level of an output audio signal that is processed by output audio processing module 214 for playback via loudspeaker(s) 216, thereby generating an estimated level of acoustic echo for each of the plurality of frequency sub-bands for each audio signal. The subtraction is performed in the log domain.

At step 404, SER calculator 222 determines a signal level for each of the plurality of frequency sub-bands for each of the audio signals generated by microphone array 202. In one embodiment, SER calculator 222 performs this function by measuring the level of an audio signal generated by each microphone in each of the plurality of frequency sub-bands.

At step 406, SER calculator 222 calculates a difference between the signal level determined in step 404 and the estimated level of acoustic echo determined in step 402 in the dB domain for each of the plurality of frequency sub-bands for each of the audio signals generated by microphone array 202. As will be appreciated by persons skilled in the relevant art(s), this operation is the mathematical equivalent of calculating a ratio between the signal level and the estimated level of acoustic echo in the linear domain for each of the plurality of frequency sub-bands for each of the audio signals generated by microphone array 202.

At step 408, audio source localization controller 210 identifies the frequency sub-bands in which the difference calculated during step 406 exceeds a threshold for every audio signal generated by microphone array 202. In one example implementation, the threshold is in the range of 6-10 decibels (dB), and in a particular example implementation, the threshold is 6 dB.

At step 410, audio source localization controller 210 selectively disables or enables audio source localization module 206 based at least on the frequency sub-bands identified during step 408. For example, in one embodiment, if the number of frequency sub-bands identified during step 408 does not exceed a threshold, then audio source localization controller 210 will disable audio source localization module 206 from generating or outputting new location information whereas if the number of frequency sub-bands identified during step 408 does exceed the threshold, then audio source localization controller 210 will enable audio source localization module 206 to generate or output new location information. In a further embodiment, if the number of frequency sub-bands identified during step 408 exceeds the threshold, then audio source localization controller 210 will enable audio source localization module 206 to generate or output new location information based only on components of the digital audio signals produced by arrays 202 and 204 that are located in the identified frequency sub-bands, since these are the frequency sub-bands that may be deemed reliable for performing audio source localization.

One advantage of the foregoing sub-band-based approach is that it can make use of both the time and frequency separation between acoustic echo and the desired components of the audio input received by microphone array 202 to render a disabling/enabling decision and to identify reliable frequency sub-bands for performing audio source localization. It is noted that other sub-band based approaches may be used than those previously described. For example, in one implementation, only certain frequency sub-bands may be considered in rendering a disabling/enabling decision or for use in performing audio source localization. In another implementation, all frequency sub-bands may be considered but the contribution of each frequency sub-band to the ultimate disabling/enabling decision and/or to the audio source localization processing may be weighted. However, these are only examples and various other approaches may be used.

Figure 5:
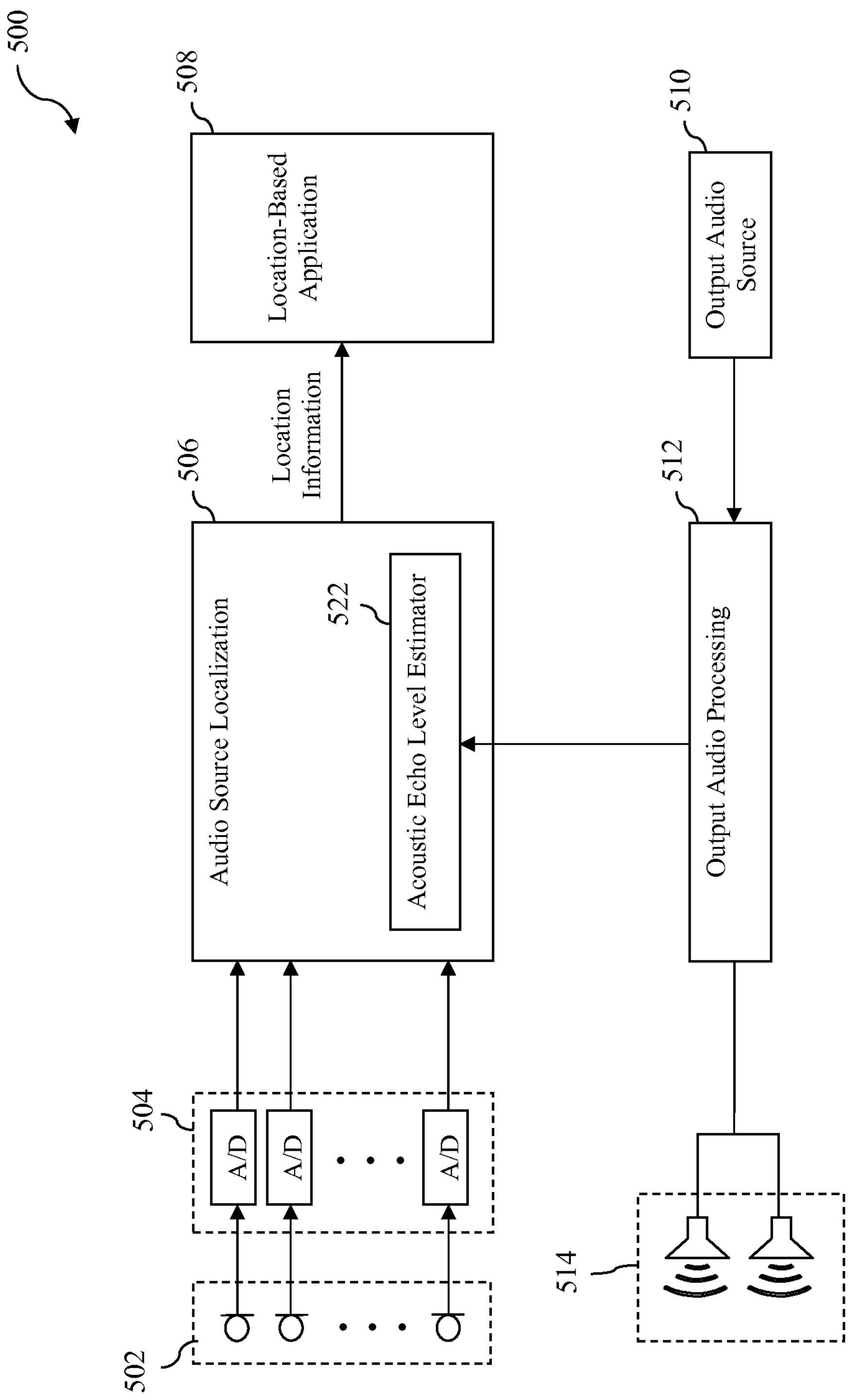
FIG. 5 is a block diagram of a second system that performs audio source localization in accordance with an embodiment of the present invention.

C. Second Example System for Performing Audio Source Localization in Accordance with an Embodiment of the Present Invention FIG. 5 is a block diagram of a second example system 500 for performing audio source localization in accordance with an embodiment of the present invention. In contrast to system 200 of FIG. 2, which uses at least one calculated SER to determine whether or not to disable or enable an audio source localization module, system 500 includes an audio source localization module that estimates a level of acoustic echo present in time-aligned segments of audio signals generated by a microphone array and then uses both the time-aligned segments and the estimated level of acoustic echo in determining the location of a desired audio source. This approach also allows system 500 to provide improved audio source localization performance in the presence of acoustic echo as compared to the conventional solutions described in the Background Section above. System 500 will now be described in more detail.

As shown in FIG. 5, system 500 includes a number of interconnected components including a microphone array 502, an array of A/D converters 504, an audio source localization module 506, a location-based application 508, an output audio source 510, an output audio processing module 512, and one or more loudspeakers 514. Each of these components will now be described.

Output audio source 510, output audio processing module 512 and loudspeaker(s) 514 are intended to represent essentially the same structures, respectively, as output audio source 212, output audio processing module 214 and loudspeaker(s) 216 as described above in reference to system 200 and are configured to perform like functions. For example, output audio processing module 512 is configured to receive an audio signal from output audio source 510 and to process the received audio signal for playback via loudspeaker(s) 514.

Microphone array 502 and array of A/D converters 504 are intended to represent essentially the same structures, respectively, as microphone array 202 and array of A/D converters 204 as described above in reference to system 200 and are configured to perform like functions. For example, each microphone in microphone array 502 operates to convert sound waves into a corresponding analog audio signal and each A/D converter in array 504 operates to convert an analog audio signal produced by a corresponding microphone in microphone array 502 into a digital audio signal comprising a series of digital audio samples prior to delivery to audio source localization logic 506.

Audio source localization module 506 is connected to array of A/D converters 504 and receives digital audio signals therefrom. Like audio source localization module 206 of system 200, audio source localization module 506 periodically processes the digital audio signals to determine a current location of a desired audio source. However, in contrast to audio source localization module 206 which may utilize a conventional audio source localization algorithm, audio source localization module 506 includes an acoustic echo level estimator 522 that estimates a level of acoustic echo present in time-aligned segments of the digital audio signals received from array 504. Audio source localization module 506 then uses both the time-aligned segments and the estimated level of acoustic echo in determining the location of a desired audio source. Acoustic echo level estimator 522 is configured to determine the estimated level of acoustic echo associated with the time-aligned segments of the digital audio signals by processing information obtained from both output audio processing module 512 and from array 504.

After determining the current location of the desired audio source, audio source localization module 506 passes this information to location-based application 508. Like location-based application 208 described above in reference to system 200, location-based application 508 is intended to broadly represent any application that is configured to perform operations based on the location information received from audio source localization module 506. Various examples of such applications have already been provided herein as part of the description of system 200 and thus will not be repeated here for the sake of brevity.

A general method by which audio source localization module 506 may operate to determine the location of a desired audio source will now be described with reference to flowchart 600 of FIG. 6. Although the method of flowchart 600 will be described herein with reference to components of example system 500, it is to be understood that the method is not limited to that implementation and may be performed by other components or systems entirely.

Figure 6:
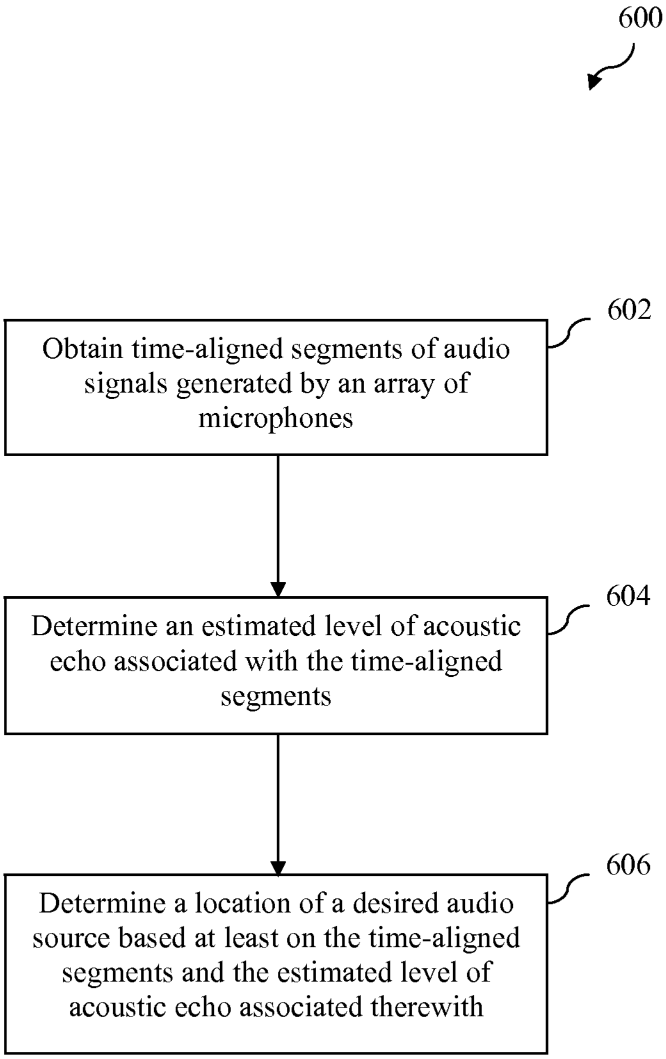
FIG. 6 depicts a flowchart of a method for determining the location of a desired audio source in accordance with an embodiment of the present invention.

As shown in FIG. 6, the method of flowchart 600 begins at step 602 in which audio source localization module 506 obtains time-aligned segments of audio signals generated by microphone array 502. These time-aligned segments may comprise, for example, time-aligned frames of the digital audio signals produced by array of A/D converters 504. Each frame may comprise a fixed number of digital samples obtained at a fixed sampling rate.

At step 604, acoustic echo level estimator 522 determines an estimated level of acoustic echo associated with the time-aligned segments obtained during step 602. In one embodiment, acoustic echo level estimator 222 performs this function by estimating an echo return loss (ERL) associated with one or more of the time-aligned segments and then subtracting in the log domain the estimated ERL from a level of an audio signal that was processed by output audio processing module 512 for playback via loudspeaker(s) 514. Various methods for determining an ERL are known in the art and thus need not be described herein. In one implementation, the level of the audio signal that was processed by output audio processing module 512 for playback via loudspeaker(s) is measured by output audio processing module 512 and passed to acoustic echo level estimator 522.

At step 606, audio source localization module 506 determines a location of a desired audio source based at least on the time-aligned segments and the estimated level of acoustic echo associated therewith. Various methods by which step 606 may be performed in accordance with various embodiments of the present invention will now be described in reference to flowcharts 700, 800, 900, 1000 and 1100 depicted in FIGS. 7, 8, 9, 10 and 11, respectively.

Figure 7:
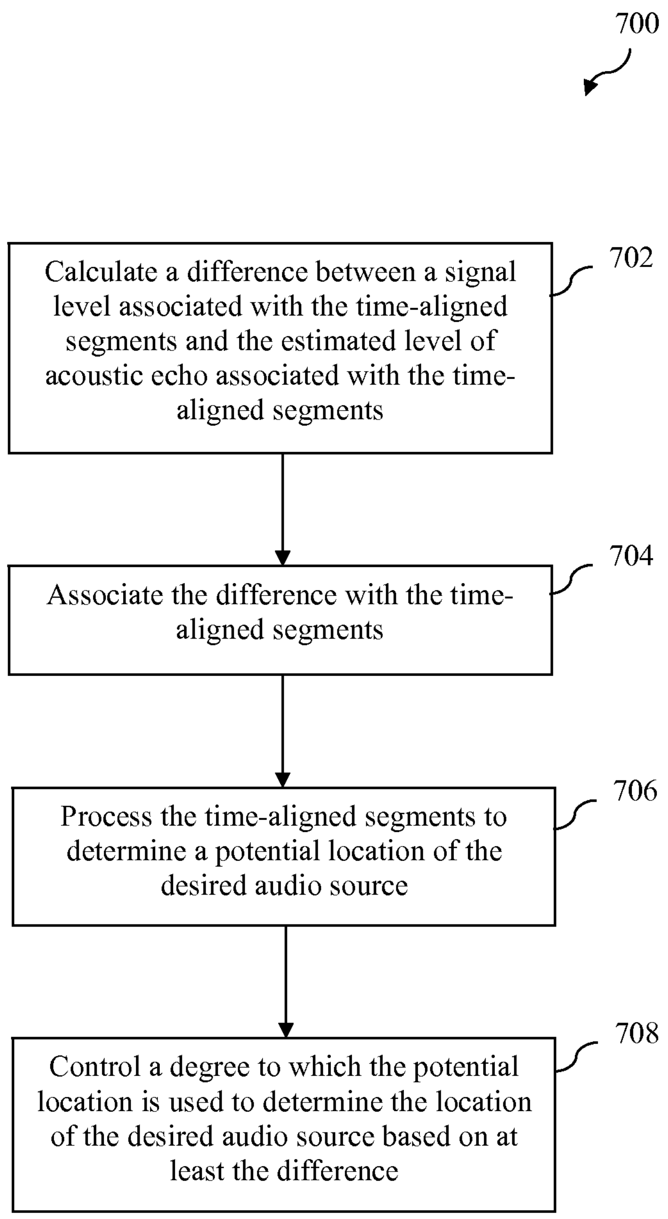
FIG. 7 depicts a flowchart of a first method for determining a location of a desired audio source based at least on time-aligned segments of audio signals generated by a microphone array and an estimated level of acoustic echo associated therewith in accordance with an embodiment of the present invention.

For example, FIG. 7 depicts a flowchart 700 of a first method for determining a location of a desired audio source based at least on time-aligned segments of audio signals generated by a microphone array and an estimated level of acoustic echo associated therewith in accordance with an embodiment of the present invention. Although the method of flowchart 700 will also be described herein with continued reference to components of example system 500, it is to be understood that the method is not limited to that implementation and may be performed by other components or systems entirely.

As shown in FIG. 7, the method of flowchart 700 begins at step 702 in which acoustic echo level estimator 522 calculates a difference between a signal level associated with the time-aligned segments and the estimated level of acoustic echo associated with the time-aligned segments in the dB domain. As will be appreciated by persons skilled in the relevant art(s), this operation is the mathematical equivalent of calculating a ratio between the signal level associated with the time-aligned segments and the estimated level of acoustic echo associated with the time-aligned segments in the linear domain. Acoustic echo level estimator 522 may obtain the signal level associated with the time-aligned segments, for example, by measuring a signal level associated with a designated one of the time-aligned segments or by calculating an average measure of the signal levels associated with two or more of the time-aligned segments.

At step 704, acoustic echo level estimator 522 associates the difference calculated during step 702 with the time-aligned segments.

At step 706, audio source localization module 506 processes the time-aligned segments to determine a potential location of the desired audio source. Any of a variety of known audio source localization methods may be used to perform this step.

At step 708, audio source localization module 506 controls a degree to which the potential location determined during step 706 is used to determine the location of the desired audio source based at least on the difference. For example, in one embodiment, audio source localization module 506 determines the location of the desired audio source based on the potential location determined during step 706 and also on one or more locations determined for one or more previously-received sets of time-aligned segments. Each of the previously-received sets of time-aligned segments is also associated with a corresponding difference. In such an embodiment, audio source localization module 506 may combine the potential location associated with the current set of time-aligned segments as determined during step 706 and the previously-determined location(s) associated with the previously-received sets of time-aligned segments in some manner to select the new location of the desired audio source. In performing the combination, audio source localization module 506 may weight the contribution of each set of time-aligned segments based on the difference associated with that set. For example, if the difference associated with a particular set of time-aligned segments is relatively low (which indicates that the segments are less reliable for performing audio source localization) then audio source localization module 506 may apply a lesser weight to the contribution of that set, whereas if the difference associated with a particular set of time-aligned segments is relatively high (which indicates that the segments are more reliable for performing audio source localization), then audio source localization module 506 may apply a greater weight to the contribution of that set. The difference associated with each set of time-aligned segments can thus advantageously be used as a "trust factor" for determining the reliability of information generated by processing each set.

Persons skilled in the relevant art(s) will readily appreciate that step 702 may be carried out in the frequency sub-band domain, such that a difference, or SER, is obtained for each frequency sub-band. In this case, in step 708, determining the degree to which the potential location is used to determine the location of the desired audio source may include, but is not limited to, considering the number of frequency sub-bands that provide what is deemed a reliable or unreliable difference, considering the differences associated with only certain frequency sub-bands, considering weighted versions of the differences associated with the frequency sub-bands, or any combination of the foregoing.

Figure 8:
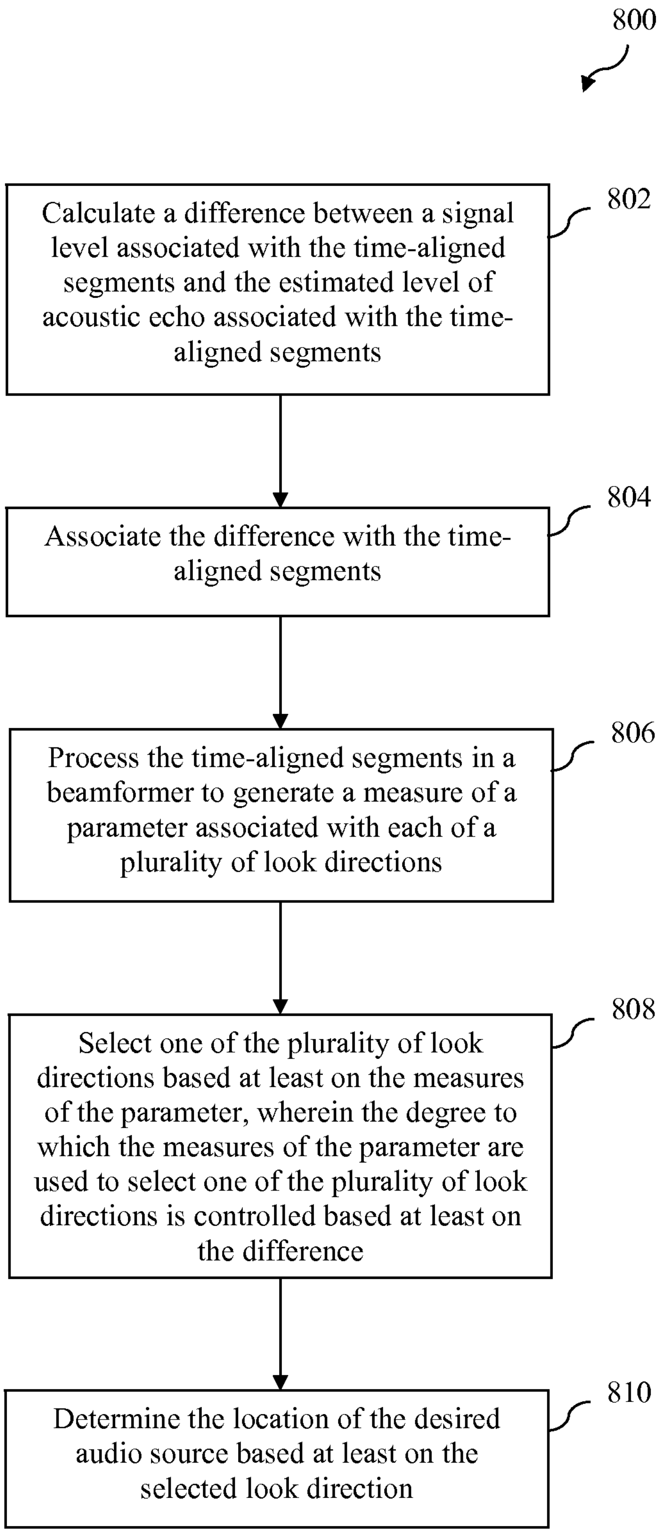
FIG. 8 depicts a flowchart of a second method for determining a location of a desired audio source based at least on time-aligned segments of audio signals generated by a microphone array and an estimated level of acoustic echo associated therewith in accordance with an embodiment of the present invention.

FIG. 8 depicts a flowchart 800 of a second method for determining a location of a desired audio source based at least on time-aligned segments of audio signals generated by a microphone array and an estimated level of acoustic echo associated therewith in accordance with an embodiment of the present invention. Although the method of flowchart 800 will also be described herein with continued reference to components of example system 500, it is to be understood that the method is not limited to that implementation and may be performed by other components or systems entirely.

As shown in FIG. 8, the method of flowchart 800 begins at step 802, in which acoustic echo level estimator 522 calculates a difference between a signal level associated with the time-aligned segments and the estimated level of acoustic echo associated with the time-aligned segments. At step 804, acoustic echo level estimator 522 associates the difference calculated during step 802 with the time-aligned segments.

These steps are intended to represent essentially the same processes that were described above in reference to steps 702 and 704 of flowchart 700.

At step 806, audio source localization module 506 processes the time-aligned segments in a beamformer to generate a measure of a parameter associated with each of a plurality of look directions. For example, if audio source localization module 506 uses the well-known Steered Response Power (SRP) approach to performing localization, then step 806 may comprise processing the time-aligned segments in a beamformer to generate a measure of response power associated with each of a plurality of look directions. As another example, if audio source localization module 506 uses an approach to localization that is described in commonly-owned, co-pending U.S. patent application Ser. No. 12/566,329 (entitled "Audio Source Localization System and Method," filed on Sep. 24, 2009, the entirety of which is incorporated by reference herein), then step 806 may comprise processing the time-aligned segments in a beamformer to generate a measure of distortion associated with each of the plurality of look directions.

At step 808, audio source localization module 506 selects one of the plurality of look directions based at least on the measures of the parameter generated during step 806, wherein the degree to which the measures of the parameter are used to select one of the plurality of look directions is controlled based at least on the difference. For example, in one embodiment, audio source localization module 506 selects the look direction based on the measures of the parameter generated during step 806 and also measures of the parameter generated for one or more previously-received sets of time-aligned segments. Each of the previously-received sets of time-aligned segments is also associated with a corresponding difference. In such an embodiment, audio source localization module 506 may combine the measures of the parameter associated with the current set of time-aligned segments as determined during step 806 and the previously-determined measures of the parameter associated with the previously-received sets of time-aligned segments in some manner to select the look direction. In performing the combination, audio source localization module 506 may weight the contribution of each set of time-aligned segments based on the difference associated with that set. The difference associated with each set of time-aligned segments can thus advantageously be used as a "trust factor" for determining the reliability of information generated by processing each set.

At step 810, audio source localization module 506 determines the location of the desired audio source based at least on the look direction selected during step 808.

Persons skilled in the relevant art(s) will readily appreciate that step 802 may be carried out in the frequency sub-band domain, such that a difference is obtained for each frequency sub-band. In this case, in step 808, determining the degree to which the measures of the parameter are used to select one of the plurality of look directions may include, but is not limited to, considering the number of frequency sub-bands that provide what is deemed a reliable or unreliable difference, considering the differences associated with only certain frequency sub-bands, considering weighted versions of the differences associated with the frequency sub-bands, or any combination of the foregoing. The measures associated with different sets of time-aligned segments may also be combined on a frequency sub-band basis, with only certain frequency sub-bands being combined, or with different weights applied to different frequency sub-bands.

Figure 9:
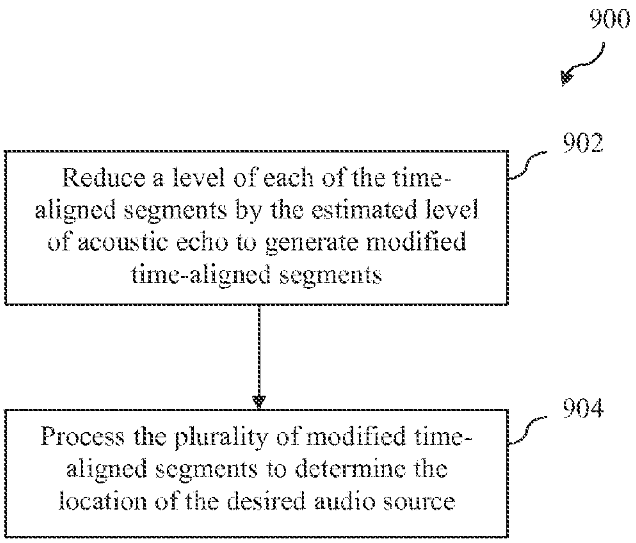
FIG. 9 depicts a flowchart of a third method for determining a location of a desired audio source based at least on time-aligned segments of audio signals generated by a microphone array and an estimated level of acoustic echo associated therewith in accordance with an embodiment of the present invention.

FIG. 9 depicts a flowchart 900 of a third method for determining a location of a desired audio source based at least on time-aligned segments of audio signals generated by a microphone array and an estimated level of acoustic echo associated therewith in accordance with an embodiment of the present invention. In contrast to the methods of flowcharts 700 and 800, which utilize an estimated level of acoustic echo to calculate a signal-to-echo ratio for a plurality of time-aligned segments and then use the ratio to weight or otherwise control the contribution of the plurality of time-aligned segments to a function used for generating a location decision, the method described in flowchart 900 actually applies the estimated level of acoustic echo to the level of the time-aligned segments directly. Although the method of flowchart 900 will also be described herein with continued reference to components of example system 500, it is to be understood that the method is not limited to that implementation and may be performed by other components or systems entirely.

As shown in FIG. 9, the method of flowchart 900 begins at step 902, in which audio source localization module 506 reduces a level of each of the time-aligned segments by the estimated level of acoustic echo as determined by acoustic echo level estimator 522 to generate modified time-aligned segments.

At step 904, audio source localization module 506 processes the plurality of modified time-aligned segments to determine the location of the desired audio source.

Figure 10:
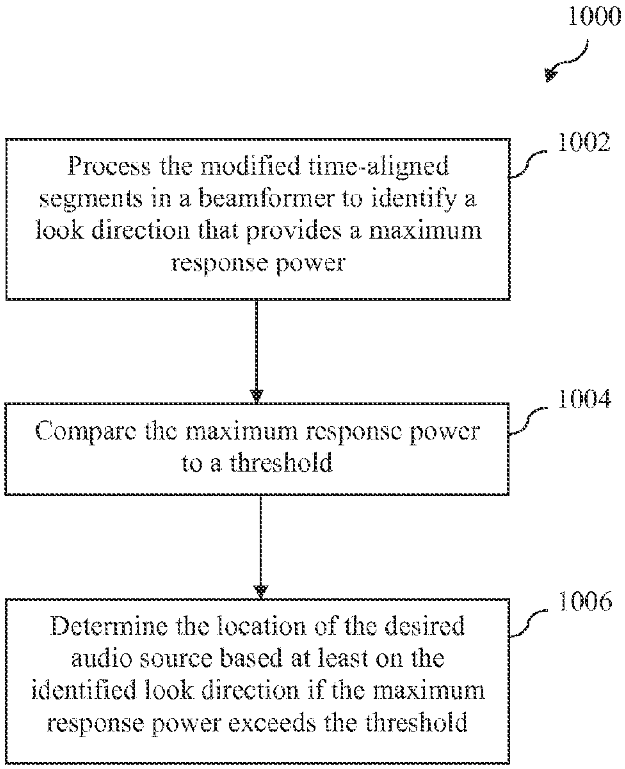
FIG. 10 depicts a flowchart of a method for processing a plurality of modified time-aligned segments of audio signals generated by an array of microphones to determine a location of a desired audio source in accordance with an embodiment of the present invention.

FIG. 10 depicts a flowchart 1000 of one method by which audio source localization module 506 may perform step 904 in an embodiment in which audio source localization module 506 uses a variant of the well known SRP-based approach for performing audio source localization.

As shown in FIG. 10, the method of flowchart 1000 begins at step 1002 in which audio source localization module 506 processes the modified time-aligned segments in a beamformer to identify a look direction that provides a maximum response power.

At step 1004, audio source localization module 506 compares the maximum response power determined during step 1002 to a threshold.

At step 1006, audio source localization module 506 determines the location of the desired audio source based at least on the look direction identified during step 1002 if the maximum response power exceeds the threshold.

In accordance with this embodiment, the level of the modified time-aligned segments that are used to generate the maximum response power will be low when the estimated level of acoustic echo is high relative to the signal level and will be high when the estimated level of acoustic echo is low relative to the signal level. By selecting the proper threshold for step 1004, this will have the beneficial effect of ignoring a selected look direction when the audio input includes a disproportionally large amount of acoustic echo and is thus unreliable.

It is noted that in the methods described in reference to flowcharts 900 and 1000, the estimated level of acoustic echo may be determined on a frequency sub-band basis. Thus, the level of the time-aligned segments can be determined for each frequency sub-band and then reduced by the estimated level of acoustic echo in the same frequency sub-band. The processing of the modified sub-bands signals can then be carried out on a frequency sub-band basis to determine the location of the desired audio source. For example, in step 1002 of flowchart 1000, the response power for each look direction can be determined on a frequency sub-band basis. Furthermore, the threshold comparison in step 1004 may be carried out on a frequency sub-band basis.

It is further noted that in the embodiment described above in reference to flowchart 1000, in which the estimated level of acoustic echo is applied directly to the level of the time-aligned segments and the modified time-aligned segments are then processed in a beamformer, it is critical that the same estimated level of acoustic echo is applied is applied to each segment. Applying a different estimated level of acoustic echo to each segment would negatively impact the beamformer since beamforming takes into account the relative magnitude and phase differences between the audio signals on each microphone channel. It is conceivable that a different estimated level of acoustic echo could be applied to each frequency sub-band when the implementation is in the frequency sub-band domain—however, the same overall estimated level of acoustic echo must be applied to all microphone channels.

Figure 11:
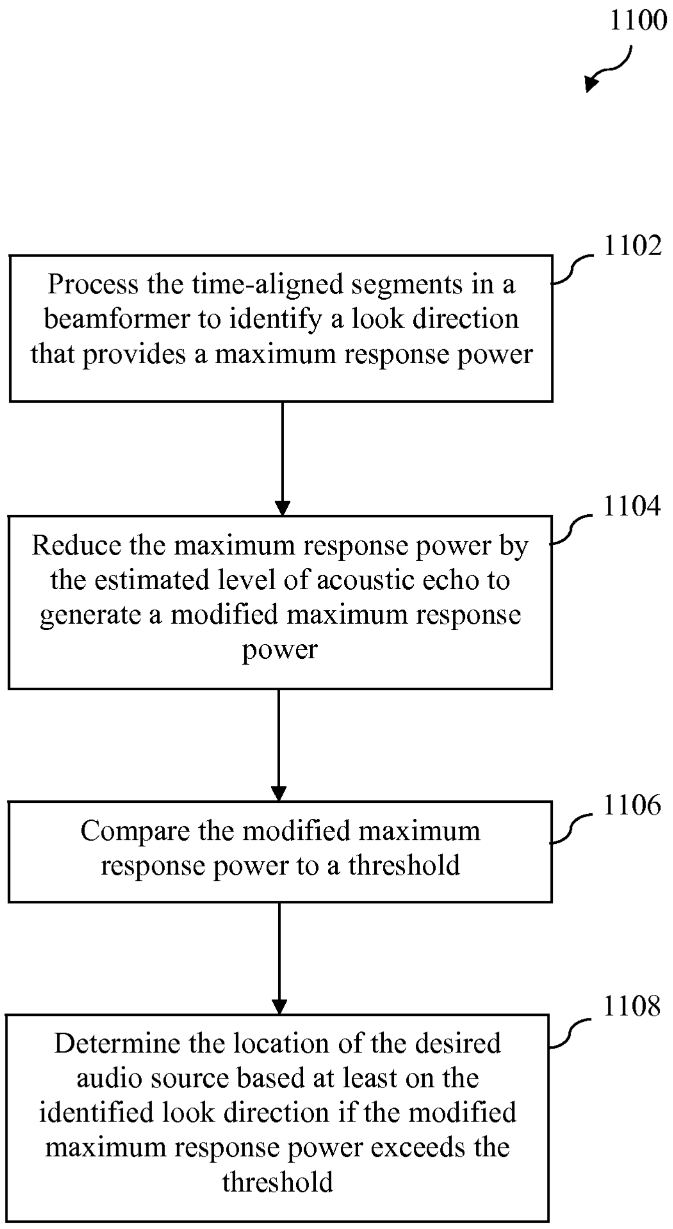
FIG. 11 depicts a flowchart of a fourth method for determining a location of a desired audio source based at least on time-aligned segments of audio signals generated by a microphone array and an estimated level of acoustic echo associated therewith in accordance with an embodiment of the present invention.

FIG. 11 depicts a flowchart 1100 of a fourth method for determining a location of a desired audio source based at least on time-aligned segments of audio signals generated by a microphone array and an estimated level of acoustic echo associated therewith in accordance with an embodiment of the present invention. The method of flowchart 1100 may be implemented in an embodiment in which audio source localization module 506 uses a variant of the well known SRP-based approach for performing audio source localization. Although the method of flowchart 1100 will also be described herein with continued reference to components of example system 500, it is to be understood that the method is not limited to that implementation and may be performed by other components or systems entirely.

As shown in FIG. 11, the method of flowchart 1100 begins at step 1102, in which audio source localization module 506 processes the time-aligned segments in a beamformer to identify a look direction that provides a maximum response power.

At step 1104, audio source localization module 506 reduces the maximum response power determined during step 1102 by the estimated level of acoustic echo as determined by acoustic echo level estimator 522 to generate a modified maximum response power.

At step 1106, audio source localization module 506 compares the modified maximum response power to a threshold.

At step 1108, audio source localization module 506 determines the location of the desired audio source based at least on the identified look direction if the modified maximum response power exceeds the threshold.

In accordance with this embodiment, the level of the modified maximum response power will be low when the estimated level of acoustic echo is high relative to the signal level and will be high when the estimated level of acoustic echo is low relative to the signal level. By selecting the proper threshold for step 1106, this will have the beneficial effect of ignoring a selected look direction when the audio input includes a disproportionally large amount of acoustic echo and is thus unreliable.

It is noted that in the method described in reference to flowchart 1100, the estimated level of acoustic echo may be determined on a frequency sub-band basis. Thus, step 1102 can encompass determining the steered response power associated with each look direction in each frequency sub-band and step 1104 can encompass reducing the steered response power associated with the identified look direction in each frequency sub-band by the estimated level of acoustic echo in the same frequency sub-band. As a result, the comparison of the maximum response power to a threshold in step 1106 can be carried out on a frequency sub-band basis if desired.

D. Example Embodiments Including Acoustic Echo Cancellers

Although example systems 200 and 500 described above in reference to FIGS. 2 and 5, respectively, did not include acoustic echo cancellers, embodiments of the present invention may also be implemented in systems that include acoustic echo cancellers. For example, FIG. 12 is a block diagram of such a system 1200.

Figure 12:
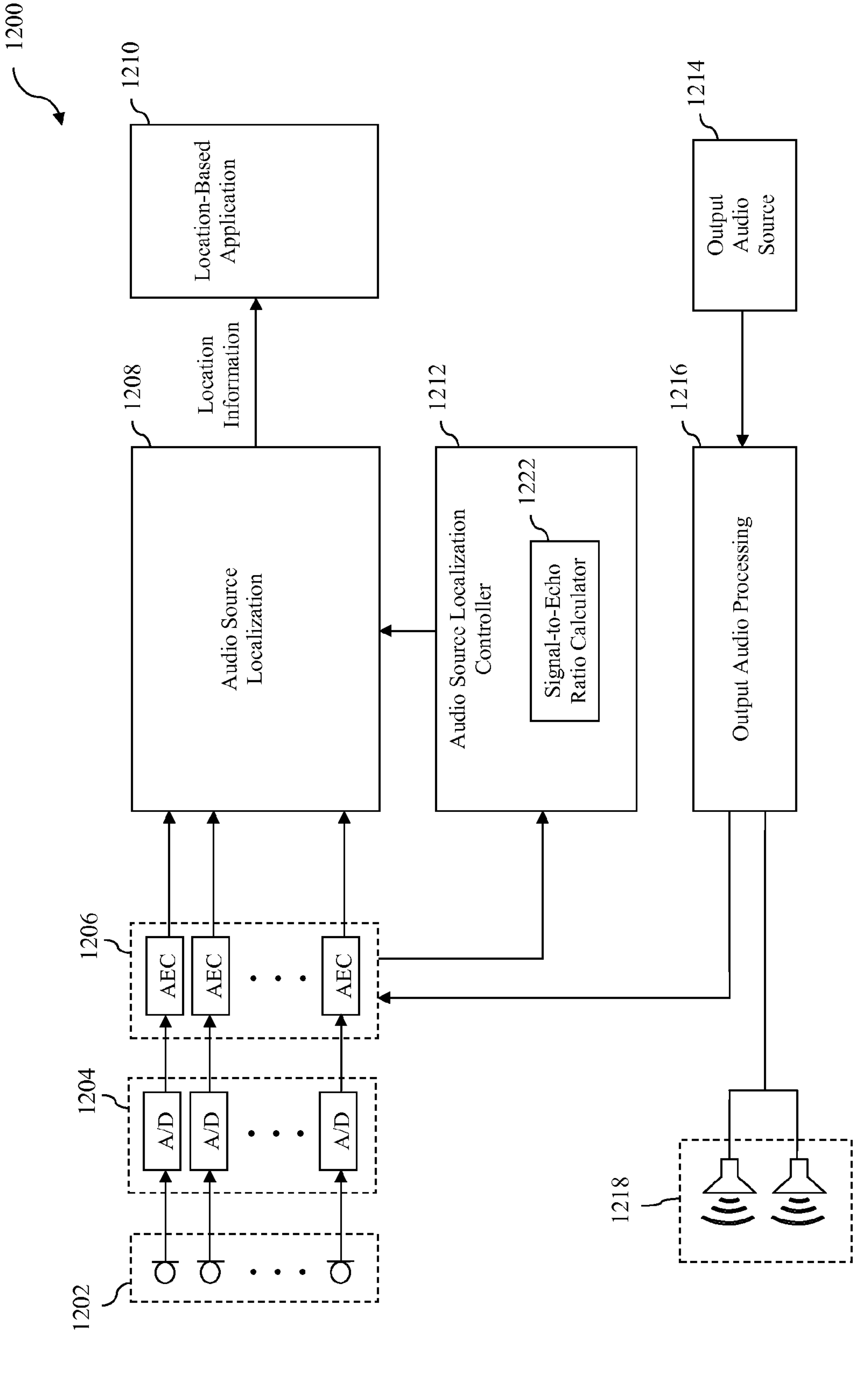
FIG. 12 is a block diagram of a first system that includes acoustic echo cancellers and performs audio source localization in accordance with an embodiment of the present invention.

As shown in FIG. 12, system 1200 includes an array of microphones 1202, an array of A/D converters 1204, a location-based application 1210, an output audio source 1214, an output audio processing module 1216 and one or more loudspeakers 1218. These components are intended to represent essentially the same structures, respectively, as array of microphones 202, array of A/D converters 204, location-based application 208, output audio source 212, output audio processing module 214 and loudspeaker(s) 216 as described above in reference to system 200 and are configured to perform like functions.

As further shown in FIG. 12, system 1200 includes an array of acoustic echo cancellers 1206 that operate to receive the digital representations of the audio signals produced by arrays 1202 and 1204 and to perform acoustic echo cancellation thereon. As will be appreciated by persons skilled in the relevant art(s), the acoustic echo cancellation function is performed based at least in part on information concerning an output audio signal processed by output audio processing module 1216. The signals generated by array 1206 are then provided to an audio source localization module 1208 which processes the signals to determine a current location of a desired audio source and passes the location information to location-based application 1210.

System 1200 also includes an audio source localization controller 1212. Audio source localization controller 1212 selectively enables audio source localization module 1208 to produce updated location information when it determines that the impact of acoustic echo upon the performance of the module is likely to be acceptable and selectively disables audio source localization module 1208 from producing updated location information when it determines that the impact of acoustic echo upon the performance of the module is likely to be unacceptable. To determine the impact of acoustic echo upon the performance of audio source localization module 1208, audio source localization controller includes an SER calculator 1222 that calculates at least one SER upon which the disabling/enabling decision is premised.

However, unlike SER calculator 222 of system 200 which determines an SER by calculating a difference in the dB domain between a signal level associated with one or more of the audio signals generated by a microphone array and an estimated level of acoustic echo associated with one or more of those signals, SER calculator 1222 determines an SER by calculating a difference in the dB domain between a signal level associated with one or more of the audio signals generated by microphone array 1202 after application of acoustic echo cancellation thereto to and an estimated level of residual echo associated with one or more of those signals after application of acoustic echo cancellation thereto.

In one embodiment, the estimated level of residual echo is determined by estimating an ERL associated with one or more of the audio signals generated by microphone array 1202 after application of acoustic echo thereto and then subtracting the ERL from the level of an output audio signal processed by output audio processing module 1216. In this case, ERL refers to the combined loss between the echo path and the echo cancellation operation. In another embodiment, the estimated level of residual echo is determined by estimating an ERL associated with one or more of the audio signals generated by microphone array 1202 and an estimate of the amount of echo cancellation that is obtained by the echo cancellers (which may be referred to as the echo return loss enhancement (ERLE)) and then subtracting the estimated ERL and ERLE from the level of an output audio signal processed by output audio processing module 1216.

Aside from the manner in which the SER is calculated as described above, the operation of system 1200 may be otherwise identical to that described above in reference to system 200 of FIG. 2 and in reference to flowcharts 300 and 400 as described above in reference to FIGS. 3 and 4. It is noted that the inclusion of acoustic echo cancellers in system 1200 of FIG. 12 may provide improved performance since the estimated level of residual echo will generally be lower than the estimated level of echo.

Figure 13:
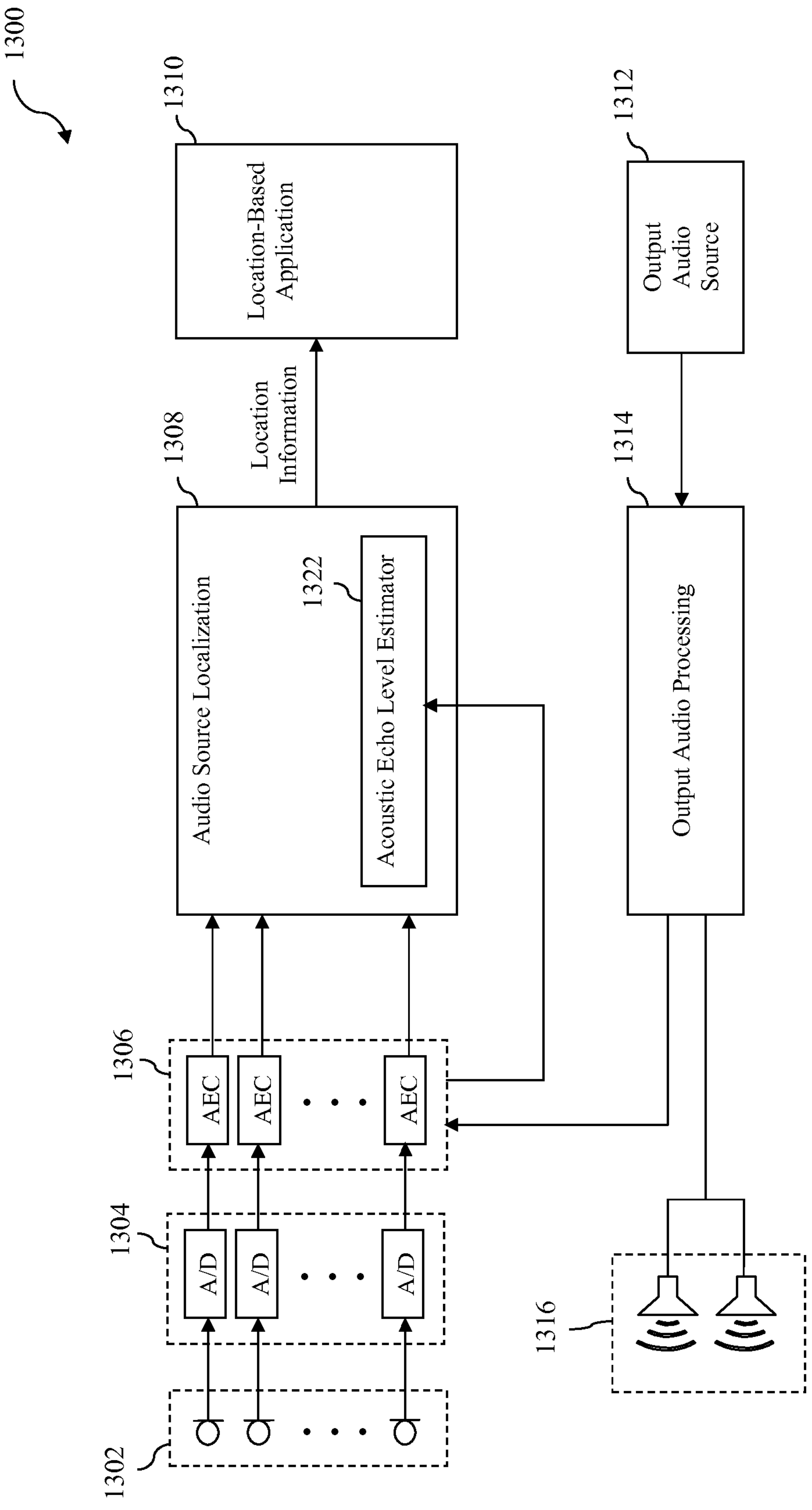
FIG. 13 is a block diagram of a second system that includes acoustic echo cancellers and performs audio source localization in accordance with an embodiment of the present invention.

FIG. 13 is a block diagram of another system 1300 that includes acoustic echo cancellers and performs audio source localization in accordance with an embodiment of the present invention. As shown in FIG. 13, system 1300 includes an array of microphones 1302, an array of A/D converters 1304, a location-based application 1310, an output audio source 1312, an output audio processing module 1314 and one or more loudspeakers 1316. These components are intended to represent essentially the same structures, respectively, as array of microphones 502, array of A/D converters 504, location-based application 508, output audio source 510, output audio processing module 512 and loudspeaker(s) 514 as described above in reference to system 500 and are configured to perform like functions.

As further shown in FIG. 13, system 1300 includes an array of acoustic echo cancellers 1306 that operate to receive the digital representations of the audio signals produced by arrays 1302 and 1304 and to perform acoustic echo cancellation thereon. As will be appreciated by persons skilled in the relevant art(s), the acoustic echo cancellation function is performed based at least in part on information concerning an output audio signal processed by output audio processing module 1314. The signals generated by array 1306 are then provided to an audio source localization module 1308 which processes the signals to determine a current location of a desired audio source and passes the location information to location-based application 1310.

Audio source localization module 1308 includes an acoustic echo level estimator 1322 that estimates a level of acoustic echo present in time-aligned segments of the digital audio signals received from array 1306. Audio source localization module 1308 then uses both the time-aligned segments and the estimated level of acoustic echo in determining the location of a desired audio source. Any of the methods described above in reference to flowcharts 600, 700, 800, 900, 1000 and 1100 of FIGS. 6, 7, 8, 9, 10 and 11, respectively, may be used to perform this function.

However, unlike acoustic echo level estimator 522 of system 500 which determines an estimated level of acoustic echo associated with the time-aligned segments of the audio signals generated by a microphone array, acoustic echo level estimator 1322 determines an estimated level of residual echo associated with the time-aligned segments of audio signals generated by microphone array 1302 after application of acoustic echo cancellation thereto. Various methods for determining an estimated level of residual echo were previously described in reference to SER calculator 1222 of system 1200. In embodiments of system 1300 in which an SER is also calculated, the signal level refers to a signal level associated with the time-aligned segments of audio signals generated by microphone array 1302 after application of acoustic echo thereto. The inclusion of acoustic echo cancellers in system 1300 of FIG. 13 may provide improved performance since the estimated level of residual echo will generally be lower than the estimated level of echo.

E. Example Computer System Implementation

It will be apparent to persons skilled in the relevant art(s) that various elements and features of the present invention, as described herein, may be implemented in hardware using analog and/or digital circuits, in software, through the execution of instructions by one or more general purpose or special-purpose processors, or as a combination of hardware and software.

Figure 14:
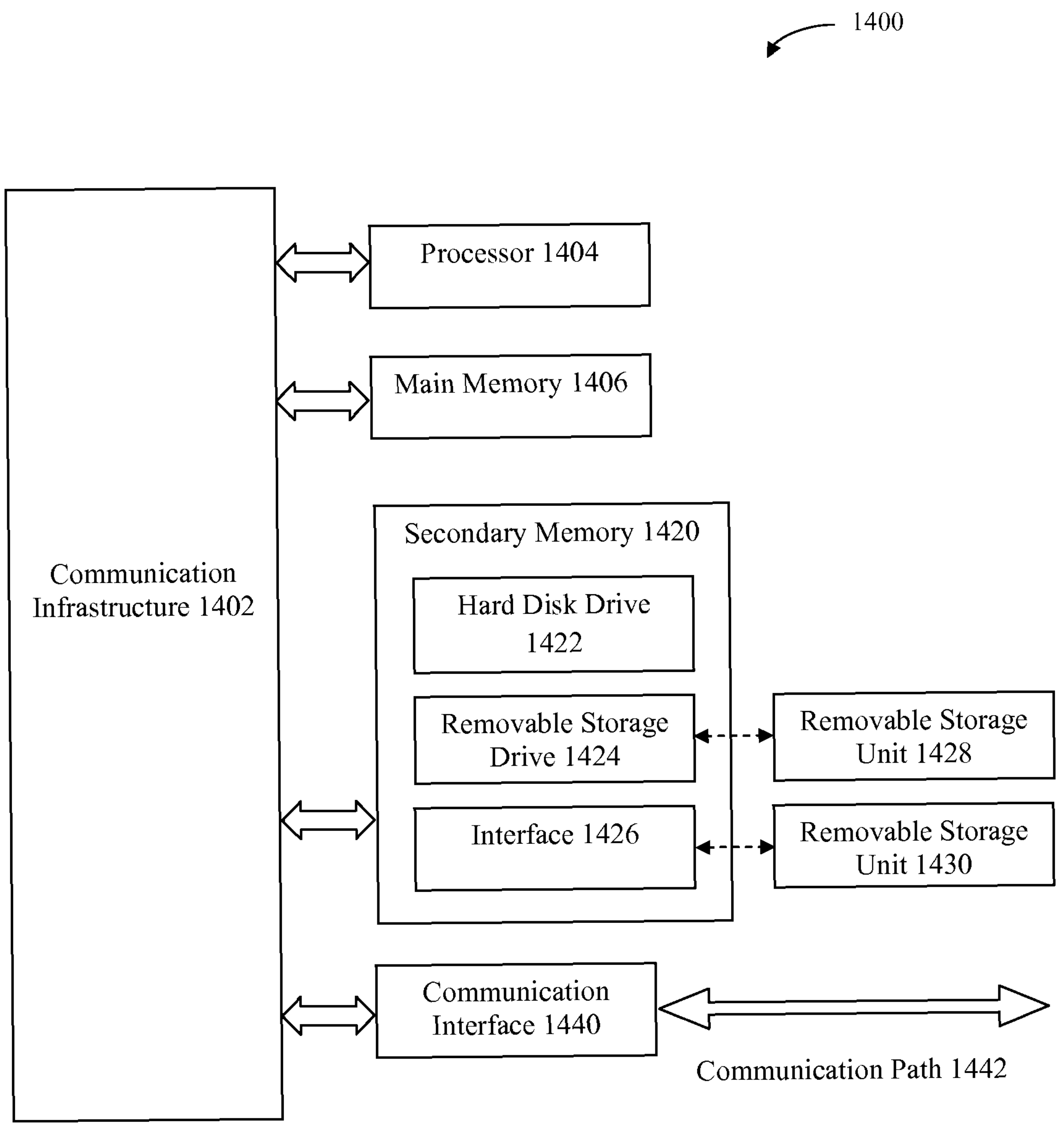
FIG. 14 is a block diagram of an example computer system that may be used to implement aspects of the present invention.

The following description of a general purpose computer system is provided for the sake of completeness. Embodiments of the present invention can be implemented in hardware, or as a combination of software and hardware. Consequently, embodiments of the invention may be implemented in the environment of a computer system or other processing system. An example of such a computer system 1400 is shown in FIG. 14. Various components depicted in FIGS. 2 and 5, for example, can execute on one or more distinct computer systems 1400. Furthermore, any or all of the steps of the flowcharts depicted in FIGS. 3, 4 and 6-11 can be implemented on one or more distinct computer systems 1400.

Computer system 1400 includes one or more processors, such as processor 1404. Processor 1404 can be a special purpose or a general purpose digital signal processor. Processor 1404 is connected to a communication infrastructure 1402 (for example, a bus or network). Various software implementations are described in terms of this exemplary computer system. After reading this description, it will become apparent to a person skilled in the relevant art(s) how to implement the invention using other computer systems and/or computer architectures.

Computer system 1400 also includes a main memory 1406, preferably random access memory (RAM), and may also include a secondary memory 1420. Secondary memory 1420 may include, for example, a hard disk drive 1422 and/or a removable storage drive 1424, representing a floppy disk drive, a magnetic tape drive, an optical disk drive, or the like. Removable storage drive 1424 reads from and/or writes to a removable storage unit 1428 in a well known manner. Removable storage unit 1428 represents a floppy disk, magnetic tape, optical disk, or the like, which is read by and written to by removable storage drive 1424. As will be appreciated by persons skilled in the relevant art(s), removable storage unit 1428 includes a computer usable storage medium having stored therein computer software and/or data.

In alternative implementations, secondary memory 1420 may include other similar means for allowing computer programs or other instructions to be loaded into computer system 1400. Such means may include, for example, a removable storage unit 1430 and an interface 1426. Examples of such means may include a program cartridge and cartridge interface (such as that found in video game devices), a removable memory chip (such as an EPROM, or PROM) and associated socket, and other removable storage units 1430 and interfaces 1426 which allow software and data to be transferred from removable storage unit 1430 to computer system 1400.

Computer system 1400 may also include a communications interface 1440. Communications interface 1440 allows software and data to be transferred between computer system 1400 and external devices. Examples of communications interface 1440 may include a modem, a network interface (such as an Ethernet card), a communications port, a PCMCIA slot and card, etc. Software and data transferred via communications interface 1440 are in the form of signals which may be electronic, electromagnetic, optical, or other signals capable of being received by communications interface 1440. These signals are provided to communications interface 1440 via a communications path 1442. Communications path 1442 carries signals and may be implemented using wire or cable, fiber optics, a phone line, a cellular phone link, an RF link and other communications channels.

As used herein, the terms "computer program medium" and "computer readable medium" are used to generally refer to media such as removable storage units 1428 and 1430 or a hard disk installed in hard disk drive 1422. These computer program products are means for providing software to computer system 1400.

Computer programs (also called computer control logic) are stored in main memory 1406 and/or secondary memory 1420. Computer programs may also be received via communications interface 1440. Such computer programs, when executed, enable the computer system 1400 to implement the present invention as discussed herein. In particular, the computer programs, when executed, enable processor 1400 to implement the processes of the present invention, such as any of the methods described herein. Accordingly, such computer programs represent controllers of the computer system 1400. Where the invention is implemented using software, the software may be stored in a computer program product and loaded into computer system 1400 using removable storage drive 1424, interface 1426, or communications interface 1440.

In another embodiment, features of the invention are implemented primarily in hardware using, for example, hardware components such as application-specific integrated circuits (ASICs) and gate arrays. Implementation of a hardware state machine so as to perform the functions described herein will also be apparent to persons skilled in the relevant art(s).

F. Conclusion

While various embodiments of the present invention have been described above, it should be understood that they have been presented by way of example only, and not limitation. It will be understood by those skilled in the relevant art(s) that various changes in form and details may be made to the embodiments of the present invention described herein without departing from the spirit and scope of the invention as defined in the appended claims. Accordingly, the breadth and scope of the present invention should not be limited by any of the above-described exemplary embodiments, but should be defined only in accordance with the following claims and their equivalents.

What is claimed is:

1. A method for performing audio source localization in a system comprising an array of microphones configured to generate a plurality of audio signals and an audio source localization module configured to process the plurality of audio signals to determine the location of a desired audio source, the method comprising:

calculating a difference between a signal level associated with one or more of the plurality of audio signals and an estimated level of acoustic echo associated with one or more of the plurality of audio signals; and selectively disabling or enabling the audio source localization module based at least on the difference.

2. The method of claim 1, further comprising:

determining the estimated level of acoustic echo associated with one or more of the plurality of audio signals by applying an estimated echo return loss to a level of an audio signal that is processed by the system for playback by one or more loudspeakers.

3. The method of claim 1, wherein the system further comprises acoustic echo cancellers configured to apply acoustic echo cancellation to the plurality of audio signals prior to processing of the plurality of audio signals by the audio source localization module and wherein calculating the difference comprises:

calculating a difference between a signal level associated with one or more of the plurality of audio signals after application of acoustic echo cancellation thereto and an estimated level of residual acoustic echo associated with one or more of the plurality of the audio signals after application of acoustic echo cancellation thereto.

4. The method of claim 1, wherein calculating the difference comprises calculating a difference for each audio signal in the plurality of audio signals between a signal level associated with the audio signal and a level of acoustic echo associated with the audio signal, and wherein selectively disabling or enabling the audio source localization module based at least on the difference comprises selectively disabling or enabling the audio source localization module based at least on the difference calculated for each audio signal.

5. The method of claim 4, wherein calculating the difference for each audio signal comprises calculating a difference for each of a plurality of frequency sub-bands for each audio signal between a signal level associated with the audio signal in the frequency sub-band and a level of acoustic echo associated with the audio signal in the frequency sub-band, and wherein selectively disabling or enabling the audio source localization module based at least on the difference calculated for each audio signal comprises selectively disabling or enabling the audio source localization module based at least on the difference calculated for each frequency sub-band for each audio signal.

6. The method of claim 5, wherein selectively disabling or enabling the audio source localization module based at least on the difference calculated for each frequency sub-band for each audio signal comprises:

identifying frequency sub-bands in which the difference exceeds a first threshold for every audio signal; and selectively disabling or enabling the audio source localization module based at least on the identified frequency sub-bands.

7. The method of claim 6, wherein selectively disabling or enabling the audio source localization module based at least on the identified frequency sub-bands comprises:

selectively disabling or enabling the audio source localization module based at least on whether the number of identified frequency sub-bands exceeds a second threshold.

8. The method of claim 7, further comprising:

when the number of identified frequency sub-band exceeds the second threshold, enabling the audio source localization module to perform audio source localization by processing only components of the plurality of audio signals located in the identified frequency sub-bands to determine the location of the desired audio source.

9. A system, comprising:

an array of microphones that generates a plurality of audio signals;

an audio source localization module that processes the plurality of audio signals to determine the location of a desired audio source; and a controller that calculates a difference between a signal level associated with one or more of the plurality of audio signals and an estimated level of acoustic echo associated with one or more of the plurality of audio signals and selectively disables or enables the audio source localization module based at least on the difference.

10. The system of claim 9, further comprising:

a plurality of acoustic echo cancellers that apply acoustic echo cancellation to the plurality of audio signals prior to processing of the plurality of audio signals by the audio source localization module;

wherein the controller calculates the difference by calculating a difference between a signal level associated with one or more of the plurality of audio signals after application of acoustic echo cancellation thereto and an estimated level of residual acoustic echo associated with one or more of the plurality of audio signals after application of acoustic echo thereto.

11. The system of claim 9, further comprising:

a location-based application that uses the determined location of the desired audio source from the audio source localization module to perform at least one operation.

12. The system of claim 10, further comprising:

an output audio processing module configured to process and generate an output audio signal;

wherein the controller is configured to determine the estimated level of residual acoustic echo associated with one or more of the plurality of audio signals by estimating an echo return loss (ERL) associated with the one or more of the plurality of audio signals and subtracting the ERL from a level of the output audio signal, or estimating an ERL associated with the one or more of the plurality of audio signals and estimating an echo return loss enhancement (ERLE) and subtracting the estimated ERL and ERLE from a level of the output audio signal.

13. A computer program product comprising a computer-readable storage device having computer control logic recorded thereon that, when executed by one or more processors, causes the one or more processors to perform operations that include:

calculating a difference between a signal level associated with one or more of a plurality of audio signals generated by an array of microphones and an estimated level of acoustic echo associated with one or more of the plurality of audio signals; and selectively disabling or enabling an audio source localization module based at least on the difference, the audio source localization module being configured to process the plurality of audio signals to determine the location of a desired audio source.

14. The computer program product of claim 13, wherein the operations further include:

determining the estimated level of acoustic echo associated with one or more of the plurality of audio signals by applying an estimated echo return loss to a level of an audio signal that is processed for playback by one or more loudspeakers.

15. The computer program product of claim 13, wherein the operations further include:

calculating a difference between a signal level associated with one or more of the plurality of audio signals after application of acoustic echo cancellation thereto and an estimated level of residual acoustic echo associated with one or more of the plurality of the audio signals after application of acoustic echo cancellation thereto.

16. The computer program product of claim 13, wherein calculating the difference comprises calculating a difference for each audio signal in the plurality of audio signals between a signal level associated with the audio signal and a level of acoustic echo associated with the audio signal, and wherein selectively disabling or enabling the audio source localization module based at least on the difference comprises selectively disabling or enabling the audio source localization module based at least on the difference calculated for each audio signal.

17. The computer program product of claim 16, wherein calculating the difference for each audio signal comprises calculating a difference for each of a plurality of frequency sub-bands for each audio signal between a signal level associated with the audio signal in the frequency sub-band and a level of acoustic echo associated with the audio signal in the frequency sub-band, and wherein selectively disabling or enabling the audio source localization module based at least on the difference calculated for each audio signal comprises selectively disabling or enabling the audio source localization module based at least on the difference calculated for each frequency sub-band for each audio signal.

18. The computer program product of claim 17, wherein selectively disabling or enabling the audio source localization module based at least on the difference calculated for each frequency sub-band for each audio signal comprises:

identifying frequency sub-bands in which the difference exceeds a first threshold for every audio signal; and selectively disabling or enabling the audio source localization module based at least on the identified frequency sub-bands.

19. The computer program product of claim 18, wherein selectively disabling or enabling the audio source localization module based at least on the identified frequency sub-bands comprises:

selectively disabling or enabling the audio source localization module based at least on whether the number of identified frequency sub-bands exceeds a second threshold.

20. The computer program product of claim 19, wherein the operations further include:

when the number of identified frequency sub-band exceeds the second threshold, enabling the audio source localization module to perform audio source localization by processing only components of the plurality of audio signals located in the identified frequency sub-bands to determine the location of the desired audio source.

* * * * *